(12) United States Patent
Andersson et al.

(10) Patent No.: US 7,507,375 B2
(45) Date of Patent: Mar. 24, 2009

(54) DEVICE FOR MEASURING COMPOUNDS IN BODY LIQUIDS

(76) Inventors: Gerhard Andersson, Ramnavägen 57, S-504 39 Boras (SE); Eva Brink, Ramnavägen 57, S-504 39 Boras (SE)

( * ) Notice: Subject to any disclaimer, the term of this patent is extended or adjusted under 35 U.S.C. 154(b) by 1114 days.

(21) Appl. No.: 10/831,261

(22) Filed: Apr. 23, 2004

(65) Prior Publication Data
US 2004/0253145 A1 Dec. 16, 2004

Related U.S. Application Data

(63) Continuation of application No. PCT/SE02/02061, filed on Nov. 12, 2002.

(30) Foreign Application Priority Data
Nov. 12, 2001 (SE) .................................. 0103763

(51) Int. Cl.
G01N 21/00 (2006.01)
G01N 33/00 (2006.01)
G07F 11/00 (2006.01)
G01N 35/00 (2006.01)
B65H 1/00 (2006.01)

(52) U.S. Cl. ............................ 422/63; 422/64; 422/65; 422/66; 422/67; 221/69; 221/79; 221/87; 221/88; 221/197; 436/43; 436/47; 436/48

(58) Field of Classification Search ................... None
See application file for complete search history.

(56) References Cited

U.S. PATENT DOCUMENTS 5,029,583 A 7/1991 Meserol et al.
5,510,266 A 4/1996 Bonner et al.

FOREIGN PATENT DOCUMENTS

EP 0 951 939 4/1999
EP 0 738 666 7/2000

*Primary Examiner*—Jill Warden
*Assistant Examiner*—Neil Turk
(74) *Attorney, Agent, or Firm*—Gauthier & Connors LLP

(57) ABSTRACT

The present invention relates to device for quantitative and/or qualitative determination of the presence/absence of a substance in a body liquid comprising a rotatably arranged magazine containing a number of test electrodes intended to be brought into contact with a body liquid to be determined, an arm arranged to influence a test electrode to a relative movement relative to said magazine, whereby the arm comprises contact sheet metals arranged to releasably be fixed to said test electrode and arranged to return said test electrode to the magazine after a finished testing, as well as an arm contained in said device.

7 Claims, 10 Drawing Sheets

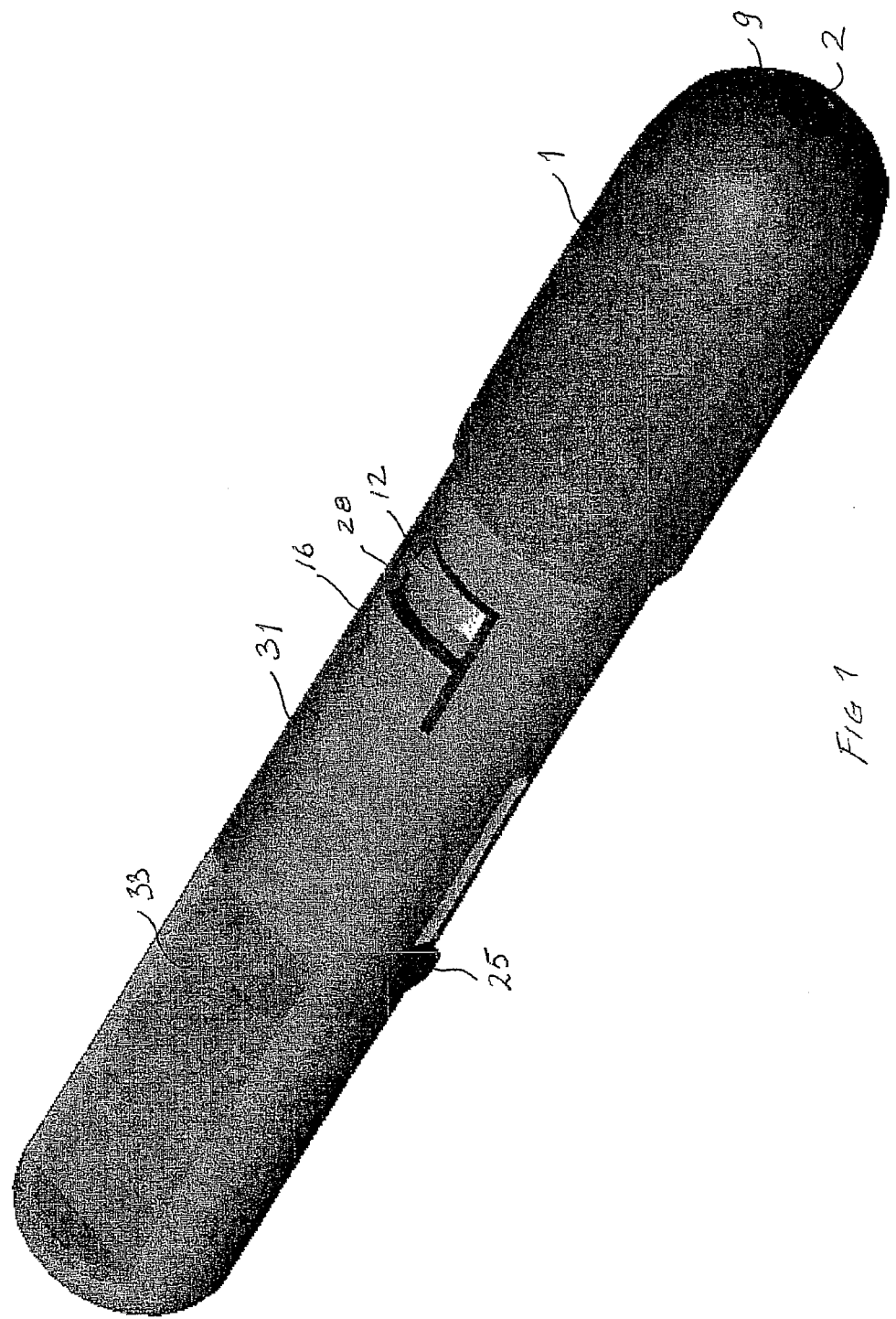

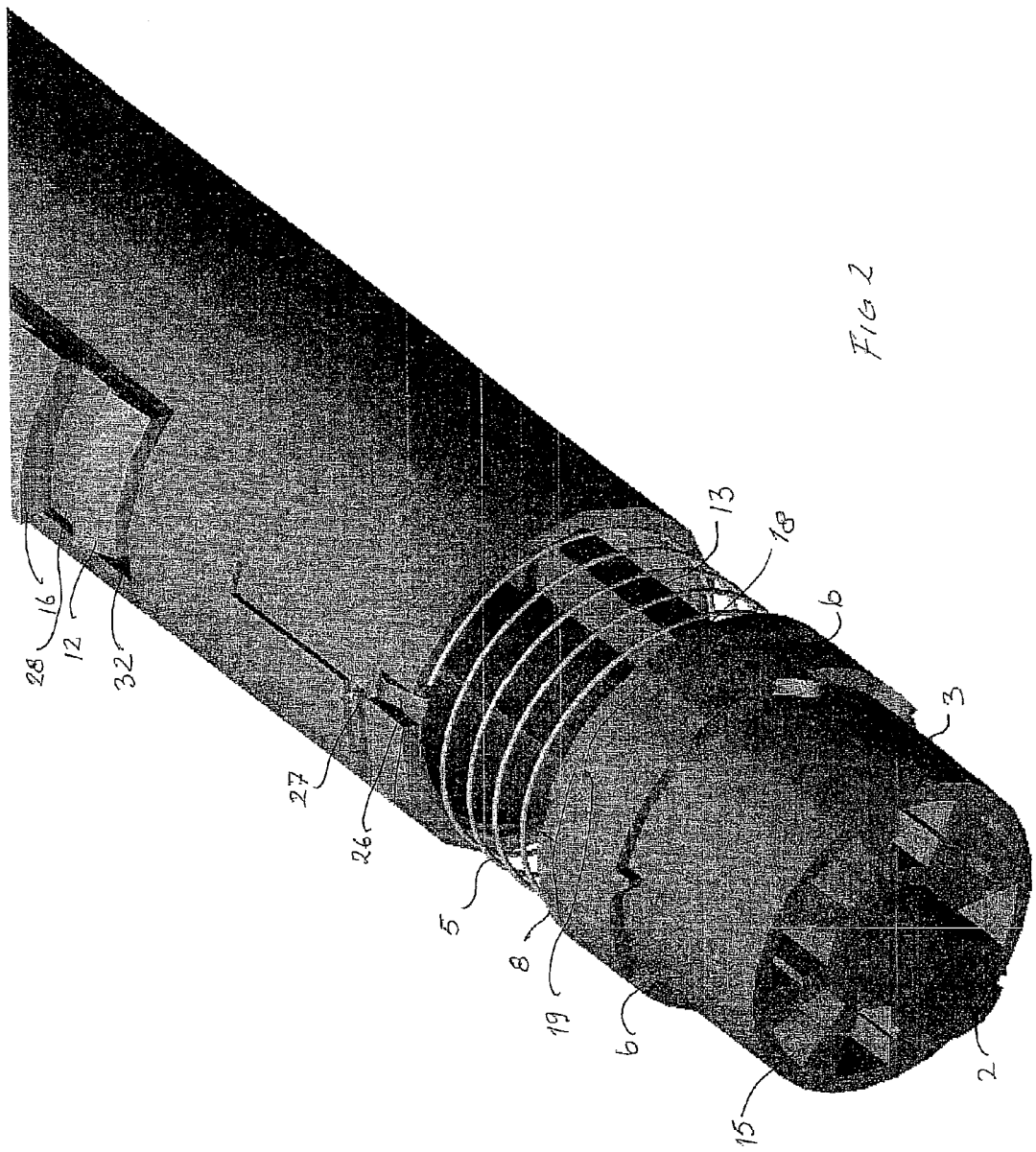

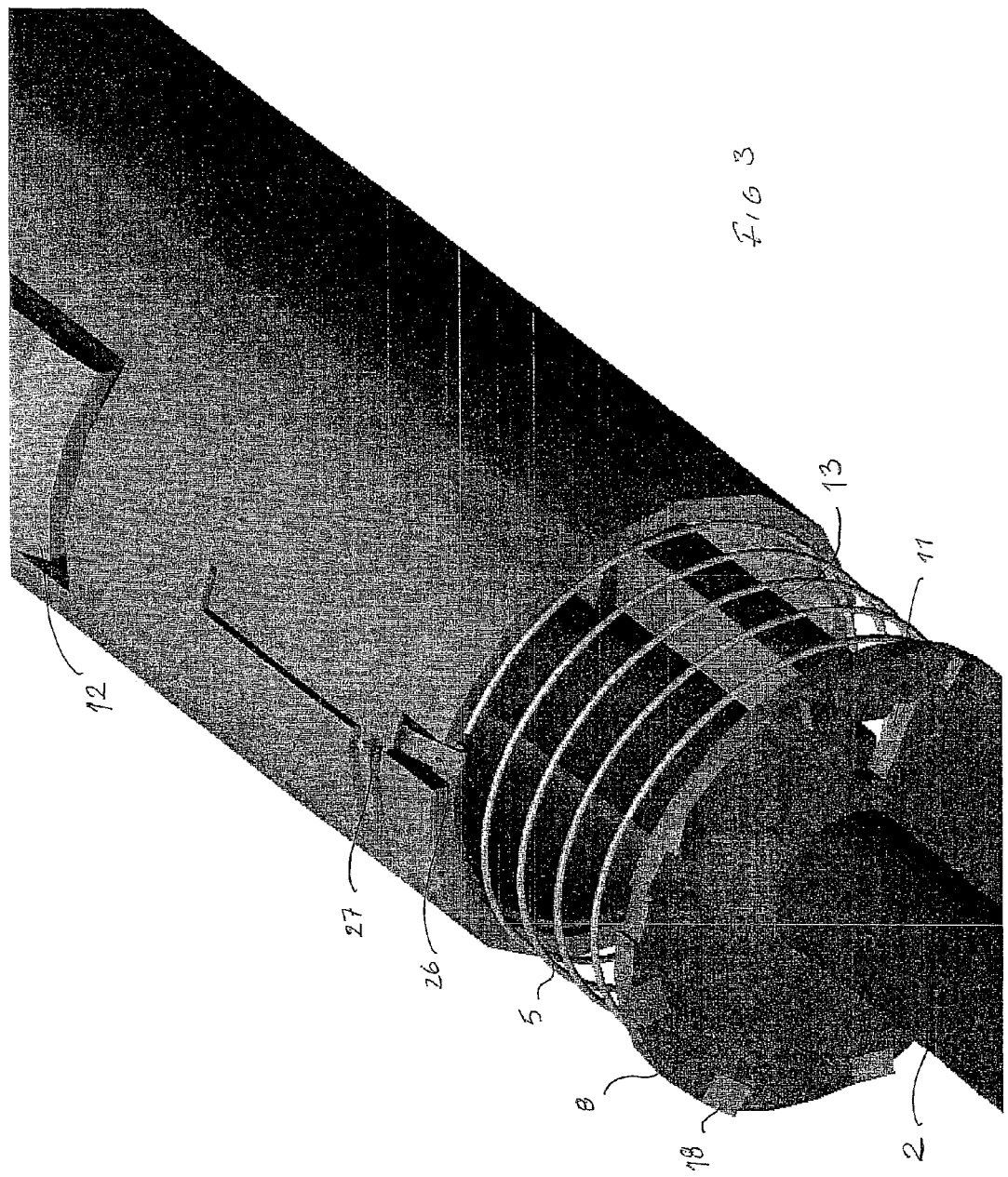

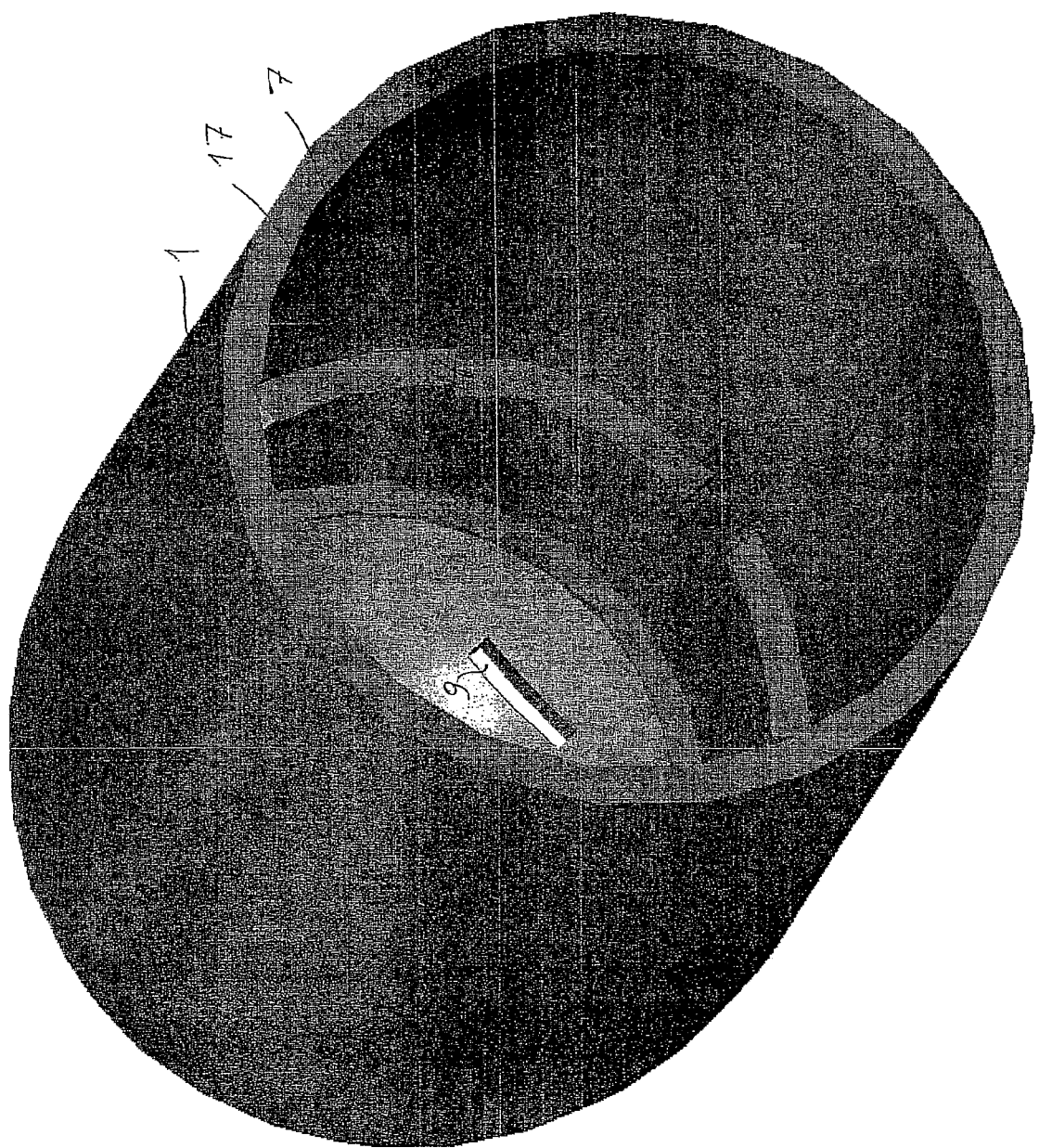

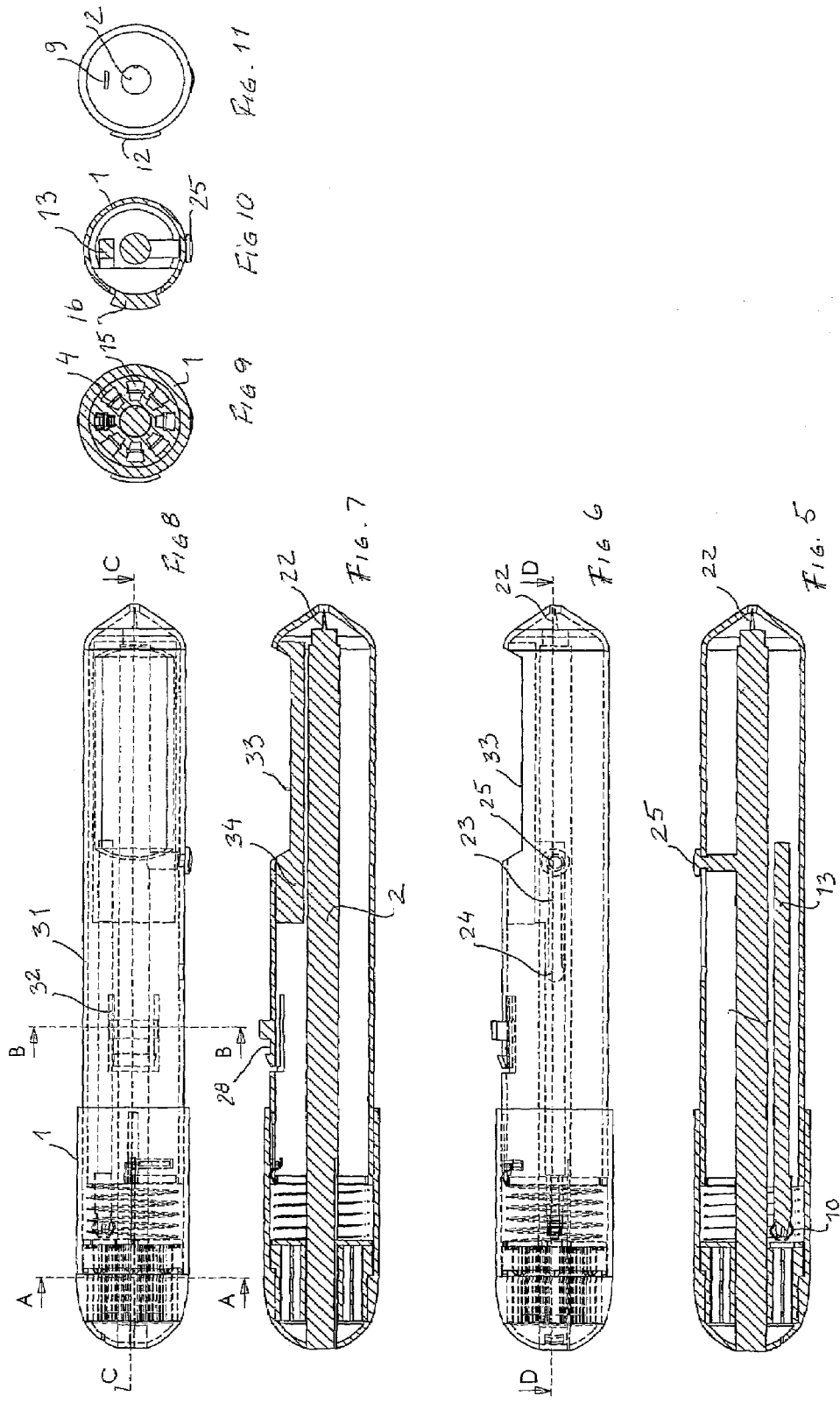

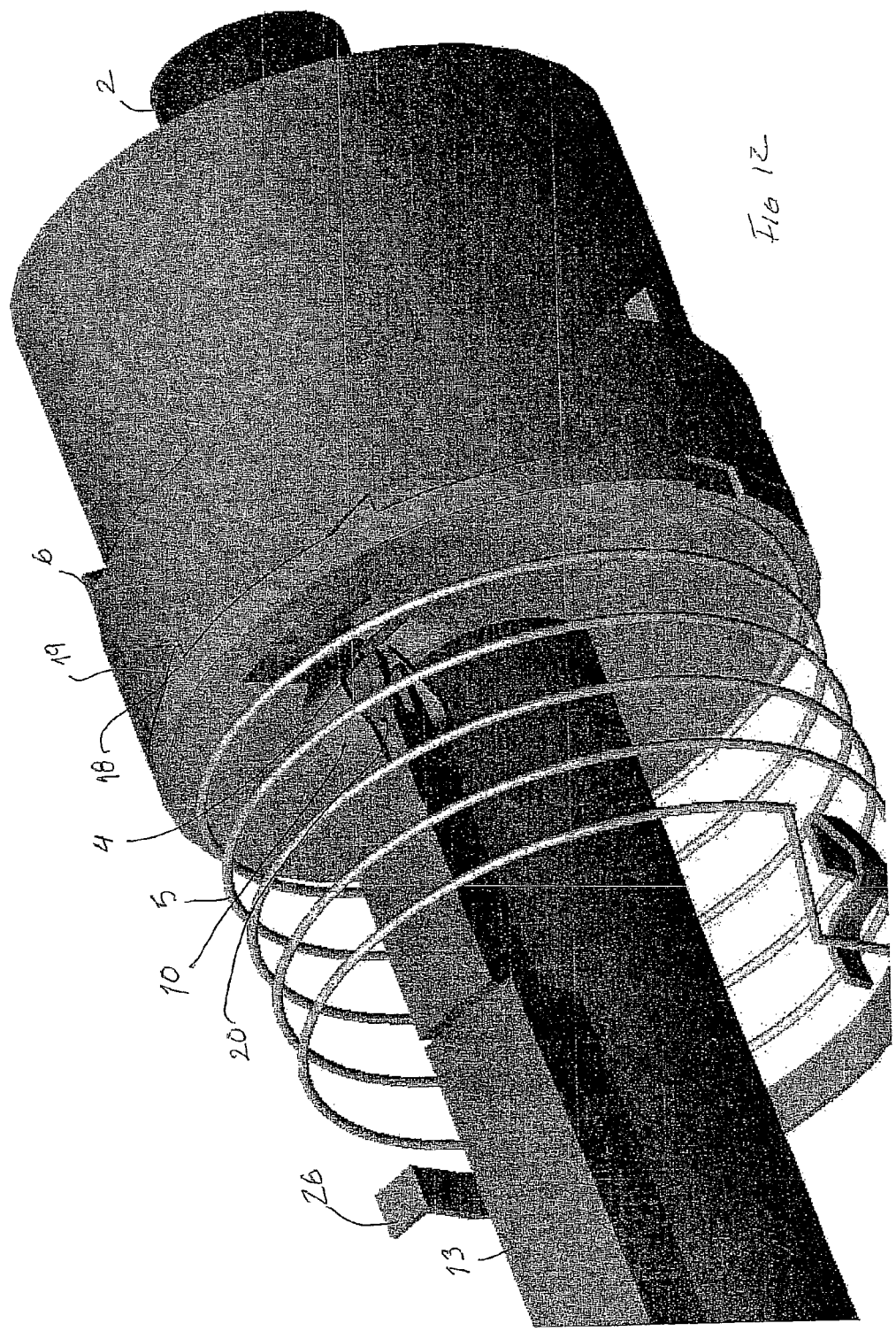

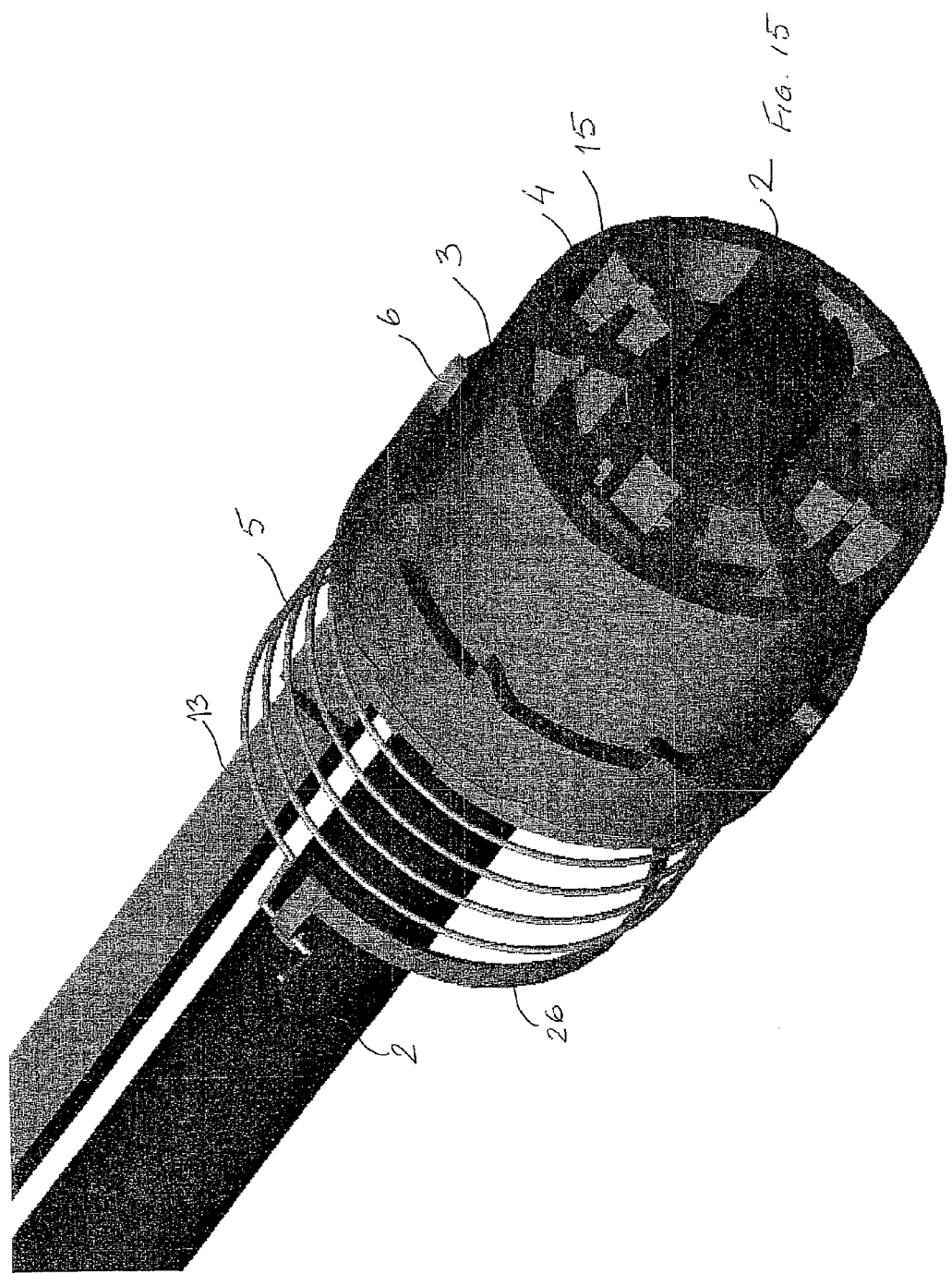

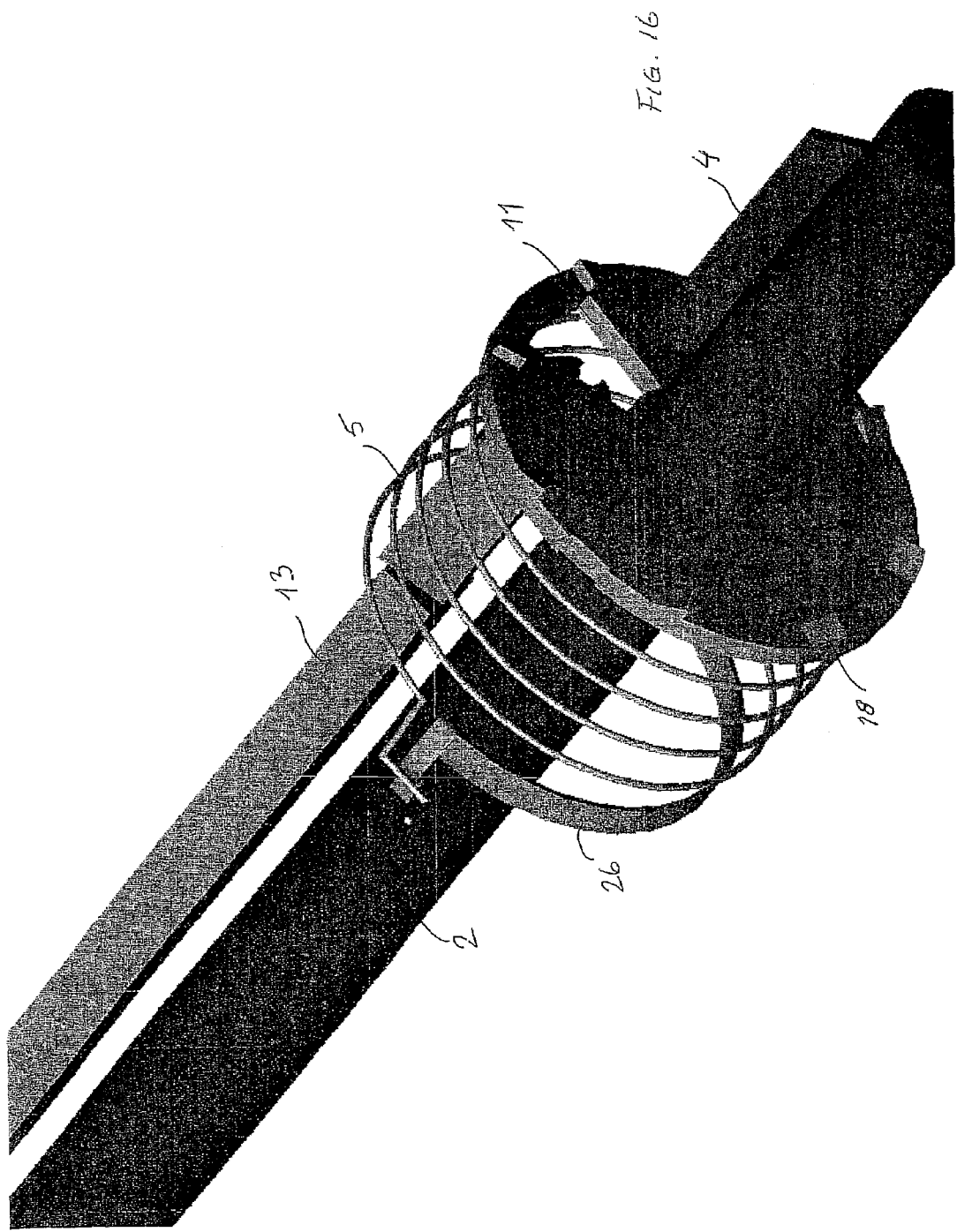

DEVICE FOR MEASURING COMPOUNDS IN BODY LIQUIDS

This is a continuation of copending application(s) International Application PCT/SE02/02061 filed on 12 Nov. 2002 and which designated the U.S.

TECHNICAL FIELD

The present invention relates to a device for measuring the presence of substances in body liquids, particularly in blood serum, such as glucose.

BACKGROUND OF THE INVENTION

At many illness conditions it is of importance to be able to show the presence or absence of a certain substance/compound in a body liquid in order to be able to provide an accurate medication.

Such an illness is diabetes where modern insulin preparations require measurement of the blood sugar concentration, glucose concentration, in order to provide for an accurate dosage of insulin in connection with e.g., a meal, before going to bed, physical activity etc., the so called personal cheque of blood glucose.

As measurement takes place on the same place every time there is often used a relatively stationary device for the determination of e.g., glucose concentration, whereby one using a mini cyvette collects a blood drip, and introduces the cyvette in a device wherein the determination is made by analysing the product. At certain determinations a chemical reaction takes place in the cyvette whereupon the reaction product is determined.

However, there is often a demand for carrying out a determination under other different situations such as when out travelling, at the office, i.e., at different places during the day, whereby one needs a portable device for such determination.

EP 0 738 666 (=U.S. Pat. No. 5,632,410) describes such a device comprising a rotating magazine containing a number of test electrodes/mini cyvettes, which rotate into position one after the other as need occurs. When measurement is to take place a test electrode is moved forward and out off the device, absorbency of a sample takes place, whereupon the test electrode is reintroduced into the device and measurement takes place, whereby the result is presented digitally on an electronic screen. After finished measurement the test electrode is thrown away out off the device. A magazine contains a number of test electrodes/mini cyvettes sufficient for the need during some days.

A similar device is also known from U.S. Pat. No. 5,510,266 whereby there is a difference in the mechanical feeding of the magazine.

Both devices show a drawback in that the test electrode/mini cyvette is thrown away after reading, which means a great risk for spreading of infections to the surroundings of body liquid worn diseases such as HIV. The problem with the reminding product is that it can land up anywhere as one throws out the test electrode.

One object of the present invention is thus to obtain a device which minimises this risk and reduces the amount of rest waste and packing.

SUMMARY OF THE PRESENT INVENTION

It has now turned out possible to be able to solve this problem by means of the present invention which alms at returning the read test electrode/mini cyvette into the magazine and store it therein.

DETAILED DESCRIPTION OF THE PRESENT INVENTION

The present invention relates to device for quantitative and/or qualitative determination of the presence/absence of a substance in a body liquid comprising a rotatably arranged magazine containing a number of test electrodes intended to be brought into contact with a body liquid to be determined, an arm arranged to influence a test electrode to a relative movement relative to said magazine and is characterized in that the arm comprises contact members arranged to releasably be fixed to said test electrode and arranged to return said test electrode to the magazine after a finished testing.

According to a further aspect of the invention it further comprises a magazine containing test electrodes placed in individual spaces for the determination of absence/presence of a substance in a body liquid and which is characterized in that the spaces receiving the test electrodes are inwardly tapering in such a way that an arm with its contact member introduced in such a space is brought to releasably grip and keep the test electrode so that this is released from said arm when being returned into said space.

According to a further aspect of the invention it comprises an arm with a contact sheet metal to be brought into contact with a test electrode whereby the arm is arranged to grip said test electrode, which preferably takes place as the arm is provided with flexible gripping claws placed on each sides of said contact sheet metals at its forward end and arranged to be able to be compressed around a contact end of a test electrode to grip the test electrode.

According to a preferred embodiment of the magazine it contains at least six spaces for test electrodes, preferably at least eight spaces for test electrodes.

By means of the present invention there is thus obtained that a test electrode/mini cyvette is returned and stored in the magazine and this may later be deposited in a safe way.

In the present invention there is used test electrodes or sensors of mini cyvette type having a generally flat rectangular form with a front, test end and a rear contact end. The sensor contains biosensing or reagent material reacting with blood sugar (glucose) or other body liquid. The test end is hereby intended to be placed in contact with the liquid to be tested, such as blood, and comprises a capillary extending from the test end into the sensor to the reagent material. The test end is placed against a blood droplet having been pressed out of a persons finger after a prick, or another body liquid, whereby the blood droplet or the liquid is sucked into the sensor by means of capillary force so that the sensor serves as a container for the liquid to be tested. The liquid is then allowed to react chemically with the reagent material in the sensor whereby an electrical signal relative to the presence of the substance to be determined, e.g., blood sugar, is obtained and is transferred to the contact member being in contact with a calculating unit providing a digital signal being read on a screen. An alternative is to read the signal optically which, however, is more difficult to meet a pure quantitative value. Other compounds, which can be determined, are proteins in urine, signalling compounds in serum, specific antibodies in serum, specific DNA-hybridisation using fluorescence determination.

To connect the electrical signals being produced at the contact end to the monitoring part, the calculation unit, the sensor shall be introduced in a sensor holder before the test end is brought into contact with the liquid to be tested. The sensor holder contains a corresponding adapted contact member, which is connected to the contact end when the sensor is connected to the holder.

Accordingly, the holder serves as a middle part between sensor and monitoring unit. The monitoring unit accumulates the values and/or analyses the result of the test performed and provides suitably a signal to a screen showing the result in digital form so that an accurate medication then can take place based upon the value obtained.

The present invention will now be described in closer detail with reference to the accompanying drawing which shows preferred embodiments, however, without being restricted to these. In the drawing FIG. 1 shows a preferred embodiment of the present invention in a perspective view, FIG. 2 shows the embodiment of FIG. 1 with an eliminated front end, FIG. 3 shows the embodiment of FIG. 1 with eliminated front end and magazine, FIG. 4 shows the front end of the embodiment of FIG. 1. In a perspective view from behind, FIG. 5 shows a cross-section of the embodiment of FIG. 1, FIG. 6 shows a lateral view of the embodiment of FIG. 1 rotated 90° around the longitudinal axis visavi FIG. 5, FIG. 7 shows a cross-section of the embodiment of FIG. 1 rotated 90° around the longitudinal axis visavi FIG. 6, FIG. 8 shows a lateral view of the embodiment of FIG. 1 rotated 90° around the longitudinal axis visavi FIG. 7, FIG. 9 shows a cross-section along the line IX-IX in FIG. 8, FIG. 10 shows a cross-section along the line X-X in FIG. 8

FIG. 11 shows an end view of the embodiment of FIG. 1,

FIG. 12 shows a detail of the embodiment of FIG. 1 comprising an arm with gripping claws, FIG. 13 shows detail of FIG. 12, FIG. 15 shows a detail of the embodiment of FIG. 1 with a magazine without any house, and FIG. 16 shows a detail of FIG. 15.

Figure 14:
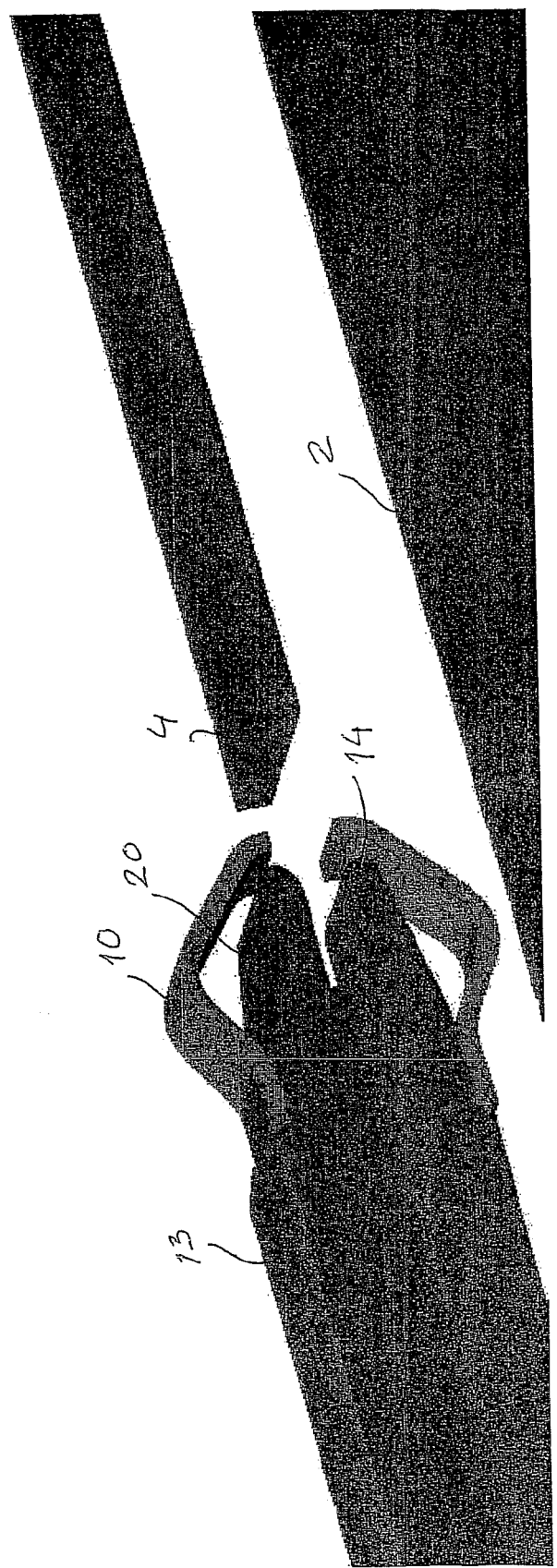
FIG. 14 shows a detail of FIG. 13 with an isolated test electrode.

The device, which generally takes the shape of a larger pen, such as 10×70 to 30×140 mm, shows a substantially cylindrical house 31 having a removable front end 1. In this front end there is a through-going, rectangular hole 9 adapted to receive a test electrode 4. The hole 9 can hereby be arranged radially or perpendicular to the radius of the front part 1. Within the device a shaft 2 runs, preferably centrally, which is arranged to receive a magazine 3 comprising spaces for receiving several test electrodes/sensors/mini cyvettes 4. The magazine 3 is cylindrically shaped having a centrally arranged hole for receiving said shaft 2. The magazine 3 is held in place onto the shaft 2 by the front end 1 which in turn is held in place by a spring 5 and by the central shaft 2 running through the centre of the front end 1. The spring 5 is partly attached to a bottom plate 8, partly attached to the cylindrical house 31 via a loop 26 arranged herein, and a fastening point 27 arranged in the cylindrical house. On the cylindrical house 31 there is a centrally arranged slot 32 having a forwardly directed hook 12 and a protruding knob 16 arranged on a resilient tongue 28 being an integrated part of the house 31. Further, in the house 31, there is an eccentrically provided shaft or arm 13 containing contact sheet metal shield 14 to be brought into contact with a rear end of a test electrode 4. The arm 13 contains a line system, as well, for transmitting information from a test electrode to an electronic unit/processing unit 34 for calculating a reaction or a determination obtained in the test electrode 4, the result of which is shown on a screen 33 at the rear end of the house 31.

When a measurement is to be carried out the front end is rotated part of a revolution corresponding to the number of test electrodes, if eight test electrodes are present in the magazine, i.e., ⅛ of a revolution, whereby the magazine 3 is driven by means of hooks 6 arranged on the outside of the magazine 3. The hooks 6 are arranged to be received by corresponding hooks 7 arranged to a hook provided ring 17 at the inside of the front end 1, whereby the magazine is driven. A bottom plate 8 provided with hooks 18 is arranged behind the magazine 3, which bottom plate also is a support surface to the spring 5. The bottom plate 8 is secured against rotation with regard to the central shaft 2, whereby, at the rotation of the magazine 3, hooks 19 present in the rear edge of the magazine snap over the hooks 18 inter alia to indication a stepping. The bottom plate 8 is also provided with a through-going hole 11 being congruent with the through-going hole 9 of the front end. After such a rotation the front end 1 is returned to its original position, whereby its inside hooks 7 snap over the hooks 6.

A non-used test electrode 4 has now been placed in the magazine in its cavity 15 and in front of said hole 9 of the front end 1. By pushing the front end 1 backwards this will become hooked onto a hook 12. Hereby the magazine 3 is brought against an arm 13 containing contact sheet metal 14 to be brought into contact with the rear contact end of the test electrode. The arm 13 simultaneously penetrates a protecting foil on the test electrode and its electrode cavity. The inlet of the cavity 15 is tapering/cone-shaped, whereby flexible gripping claws 10 arranged to the arm 13 are arranged to be compressed and grip and fix the test electrode 4 and whereby contact metal sheets 14 arranged in the test electrode receiving unit 20 of the front end of the arm 13, are brought into contact with the contact end present in the test electrode. In this position the test electrode is in a testing position per se, but does not extend out of the device. The front end 1 is subsequently moved rearward above the fastening hook 12, whereby the front point of the test electrode 4 is guided out of the hole 9. The test electrode can now receive a test droplet.

When the test has been finished, which takes less than a minute, one pushes on the knob 16 arranged to the hooking hook 12 of the front part 1, whereby the front end 1 is released and moves forward to its original position and whereby simultaneously the test electrode is moved into the magazine by means of the arm 13. The arm 13 with its contact sheet metals 14 is hereby released from the test electrode as the gripping claws 10 due to material flexibility are released from the test electrode.

The device may suitably in its rear end, in the case it is intended for testing of blood, receive a lancet device 21 comprising a spring loaded lancet 22, a tension spring 23 and a hooking member 24 with a release member 25. In order to penetrate the skin the lancet 22 is moved backwards and is tighten to the hooking member 24, whereby the rear end of the device is brought into contact with a finger pad, the release member 25 is actuated whereby the lancet is moved forward by means of the spring force and penetrates the pad to such a depth that blood penetrates. The device is then turned around so that the point of the test electrode can suck blood from the pad.

Further, the magazine may contain a drying agent in connection with the respective space for a test electrode, in those cases the test reagent is moisture sensitive and/or one utilises the meter in humid environments. The drying agent may then be present on a strip in the space or be in the form of a grain in side space communicating with the space.

| Reference numbers | |
|---|---|
| 1 | Front end |
| 2 | Central axis |
| 3 | Magazine |
| 4 | Test electrode |
| 5 | Spring |
| 6 | Hook |
| 7 | Hook |
| 8 | Bottom plate |
| 9 | Hole |
| 10 | Gripping claw |
| 11 | Through-going hole |
| 12 | Hook |
| 13 | Arm |
| 14 | Contact sheet metal |
| 15 | Cavity |
| 16 | Knob |
| 17 | Hook provided ring |
| 18 | Hook |
| 19 | Hook |
| 20 | Test electrode receiving unit |
| 21 | Lancet device |
| 22 | Lancet |
| 23 | Tension spring |
| 24 | Hooking member |
| 25 | Release member |
| 26 | Loop |
| 27 | Fastening point |
| 28 | Flexible tongue |
| 29 | |
| 30 | |
| 31 | Cylindrical house |
| 32 | Slot |
| 33 | Screen |
| 34 | Electronic unit |

The invention claimed is:

1. A device for quantitative and/or qualitative determination of the presence/absence of a substance in a body liquid comprising a rotatably arranged magazine, provided on a centrally located shaft, containing a number of test electrodes intended to be brought into contact with a body liquid to determine the presence/absence of a substance of the body liquid, an arm eccentrically arranged along the shaft and opposing said magazine to move a test electrode to a position relative to said magazine, wherein the arm comprises contact sheet metals arranged to be releasably fixed to said test electrode and arranged to return said test electrode to the magazine after a finished determination.

2. A device according to claim 1, wherein the arm with its contact sheet metals is arranged to be brought into contact with a test electrode, whereby the arm is arranged to grip said test electrode.

3. A device according to claim 2, wherein the arm at its front end is provided with flexible gripping claws placed on either side of said contact sheet metals and arranged to be able to be compressed around a contact end of a test electrode to grip the test electrode.

4. A device according to claim 3, wherein said test electrodes contained in said magazine are placed in individual spaces for the determination of absence/presence of a substance in a body liquid, wherein the spaces receiving the test electrodes are inwardly tapering in such a way that said arm with its contact sheet metals introduced in such a space is brought to releasably grip and keep the test electrode so that the test electrode is released from said arm when being returned into said space.

5. A device according to claim 4, wherein the magazine contains at least six spaces for test electrodes.

6. A device according to claim 5, wherein the magazine contains at least eight spaces for test electrodes.

7. A device according to claim 1, wherein said arm comprises a front end provided with a test electrode receiving unit containing said contact sheet metals and flexible gripping claws placed on each side of said contact sheet metals at its forward end and arranged to be able to be compressed around a contact end of a test electrode to grip and retain a test electrode.

* * * * *